(12) United States Patent
Akilesh et al.

(10) Patent No.: US 7,822,556 B2
(45) Date of Patent: Oct. 26, 2010

(54) EXPRESSION DATA ANALYSIS SYSTEMS AND METHODS

(75) Inventors: Shreeram Akilesh, Bangor, ME (US); Derry Roopenian, Salisbury Cove, ME (US); Daniel J. Shaffer, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 0 days.

(21) Appl. No.: 12/511,493

(22) Filed: Jul. 29, 2009

(65) Prior Publication Data

US 2010/0023272 A1 Jan. 28, 2010

Related U.S. Application Data

(63) Continuation of application No. 10/835,541, filed on Apr. 29, 2004, now abandoned.

(60) Provisional application No. 60/466,362, filed on Apr. 29, 2003.

(51) Int. Cl.
*G01N 33/50* (2006.01)
(52) U.S. Cl. .................... 702/19; 435/1; 435/6
(58) Field of Classification Search ............... None
See application file for complete search history.

(56) References Cited

U.S. PATENT DOCUMENTS

| | | | |
|---|---|---|---|
| 6,180,349 B1 | 1/2001 | Ginzinger et al. | |
| 6,263,287 B1 | 7/2001 | Zheng et al. | |
| 2002/0103604 A1 | 8/2002 | Liu et al. | |
| 2003/0190689 A1 | 10/2003 | Crosby et al. | |
| 2006/0129331 A1 | 6/2006 | Akilesh et al. | |

FOREIGN PATENT DOCUMENTS

| | | |
|---|---|---|
| EP | 1 037 158 A2 | 9/2000 |
| EP | 1 138 783 A2 | 10/2001 |
| WO | WO-99/54510 | 10/1999 |
| WO | WO-02/08461 A2 | 1/2002 |
| WO | WO-02/08461 A3 | 1/2002 |

OTHER PUBLICATIONS

Bilban et al. (Current issues in Mol. Biol., vol. 4, p. 57-64).*
Tseng, et al., *Issues in cDNA microarray analysis: quality filtering, channel normalization, models of variations and assessment of gene defects*, Nucleic Acid Research, vol. 12 (29), 2549-2557 (2001).
Hamalainen, et al., "Identification and Validation of Endogenous Reference Genes for Expression Profiling of T Helper Cell Differentiation by Quantitative Real-Time RT-PCR", Analytical Biochemistry 299, 63-70 (2001).
Zhang, et al., "Selection of normalizer genes in conducting relative gene expression analysis of embryos", Birth Defects Research (part A), 67:533-544 (2003).
Claverie, "Computational methods for the identification of differential and coordinated gene expression", Human Molecular Genetics, vol. 8, 1821-1832 (1999).
Zien, et al., "Centralization: a new method for the normalization of gene expression data", Bioinformatics, vol. 17 Suppl. 1, S323-331 (2001).
Jo Vandesompele, et al., "Accurate normalization of real-time quantitative RT-PCR data by genometric averaging of multiple control genes", Genome Biology, 3(7) 1-12 (2002).
Akilesh, et al., "Global pattern recognition, a software algorithm for gene expression analysis", http://www.jax.org/staff/roopenian/labsite/gene_expression.html, updated Jul. 8, 2003.
Akilesh, et al., "Customzied molecular phenotyping by quantitative gene expression and pattern recognition analysis", Genome Research, 13(7):1719-1727 (2003).
International Search Report from PCT/US2007/002167, Mar. 11, 2008.
Ginzinger, "Gene quantification using real-time quantitative PCR: An emerging technology hits the mainstream", Experimental Hematology, 30:503-512 (2002).
Suzuki, et al., "Comparative study between DNA copy nubmer abberations determined by quantitative microsatellite analysis and clinical outcome in patients with Stomach cancer", Clinical Cancer Research, 10:3013-3019 (2004).

* cited by examiner

*Primary Examiner*—Karlheinz R Skowronek
(74) *Attorney, Agent, or Firm*—McDermott Will & Emery LLP

(57) ABSTRACT

Methods and applications of Global Patter Recognition (GPR), including a system for analyzing the results of real-time polymerase chain reaction (RT-PCR) experiments employing micro-titer and/or microarray plates and robotic plate readers is described. The system employs a set of self-normalizing housekeeping primers or oligonucleotides on the plates/arrays and an algorithmic approach to normalizing expression data from all primers on the plate based on the reaction products of several of the self-normalizing gene primers oligonucleotides. Normalization is accomplished using simplex reactions involving these self-normalizing primers/oligonucleotides; the normalization parameters are then useable across all control and experimental reactions of the plate/array. A ranked list of genes whose amount of change is statistically significant can be determined. The accuracy of this list is enhanced by the data normalization aspect of the system. Other applications of GPR are also disclosed herein.

9 Claims, 7 Drawing Sheets

DATA ENTRY SHEET FOR GPR

Fig. 2

GPR OUTPUT PAGE FOR KRN ARTHRITIS DATASET

EXPRESSION DATA ANALYSIS SYSTEMS AND METHODS

RELATED APPLICATIONS

This application is a continuation of U.S. application Ser. No. 10/835,541, filed Apr. 29, 2004, which claims the benefit of U.S. provisional application 60/466,362, filed Apr. 29, 2003. The entire teachings of all above-referenced applications are incorporated herein by reference.

REFERENCE TO GOVERNMENT CONTRACTS

This invention was made with Government support awarded by the National Institutes of Health under Contract Nos. RO-1-DK-56597, RO-1-HL-65749and RO-1-A1-28802. The Government has certain rights in this invention.

BACKGROUND

Recent technological advances have enabled detailed and expansive studies of dynamic systems. For example, gene expression profiling promises to provide insight into normal biological and pathological disease processes and as such is being intensely pursued by industry and academia alike. The hope is that knowledge obtained from gene expression patterns will predict disease outcome or suggest individualized courses of therapy. While profiling at the protein level is ultimately most desirable, monitoring gene expression at the transcript level is more readily amenable with current technology. The two technologies that have emerged as the most promising gene expression tools are hybridization-based microarrays and quantitative real-time RT-PCR analysis (QPCR). With RT-PCR, Real-Time chemistries allow for the detection of PCR amplification during the reaction. Measuring the kinetics of the reaction in the early phases of PCR provides distinct advantages over traditional PCR detection, including speed and reliability of data.

Microarrays also have the advantage that they permit the simultaneous analysis of a large number of genes. Unfortunately, microarrays are not readily amenable to extensive replicate sampling because microarray analysis is labor intensive, technically demanding and requires large quantities of hybridization nucleic acid. Additionally, data interpretation is limited by the nuances of DNA hybridization kinetics and other systemic sources of error. Thus, gene expression arrays are presently best suited for prospective gene "mining," identification of sets of genes with putative expression changes that should be independently verified and more accurately quantitated by techniques such as QPCR.

QPCR systems provide sensitive and reproducible expression quantification from small amounts of starting material (RNA, mRNA, or cDNA), but have been limited in the number of genes that can be practically analyzed. In contrast to microarrays, QPCR is best suited to accurate quantification of the direction and magnitude of change in a narrow set of genes. QPCR-based approaches derive changes in gene expression by normalizing the expression of a gene against the expression of an appropriate housekeeping gene.

However, these and other applications have been limited by conventional analytical methods, which typically include subtraction methods in which "before" and "after" data points are compared and the changed regions are identified. These methods typically use only a single before and after image, thereby providing no statistical basis to account for image acquisition variability or other forms of image noise.

For example, gene expression studies apply relative normalization techniques that assume that the level of expression of a normalizer gene is invariant. This is not always the case. Studies have reported that the expression of several commonly employed normalizer genes varies by tissue type and changes in response to experimental manipulations. However, even though there is a lack of absolutely reliable normalization, this relative or comparative normalization is the only viable option currently available to investigators pursuing QPCR analyses. The alternative, absolute quantification against a titration of standards, is both labor intensive and impractical for scale-up. Conventional image change analytical methods and other methods are also similarly limited.

Accordingly, there is a need in the art for methods and systems that will allow for the application of QPCR to a number of genes to identify those genes that are varying in a significant manner.

Broadly speaking, there is also a need in the art to apply gene-expression analysis techniques to larger-scale physical problems.

SUMMARY

Global Pattern Recognition (GPR) techniques are available to assist in analyzing complex physiological and other scientific problems. In certain embodiments, such techniques are applied to the analysis of PCR and other gene expression data. To more reliably evaluate expression changes, in for example QPCR data, the systems and methods described herein are used to process datasets of data to identify statistically significant changes in gene expression patterns. By looking for a pattern of change, such systems provide more reliable detection of, for example, biological relevance. Moreover, such systems reduce or eliminate the primary reliance on single gene normalization by using multiple points of reference (normalizers) to establish a gene expression landscape to facilitate identification of changes.

More specifically, the methods described herein enable one to analyze the expression data of multiple genes. Control samples and experimental samples are prepared, and in preferred embodiments, genes that are uninformative are discarded. The expression activity of the genes is analyzed to identify a set of multiple genes that can be used as normalizers. The genes are then normalized against this identified set of genes. The normalized expression for gene of interest is then compared, such as by a T-test, so that experimental data is compared with control data. If a normalized gene pair varies significantly between the control group and the experimental group, then this is noted by incrementing a confidence parameter that represents the likelihood that the respective gene is biologically relevant in this experiment. As each gene-normalizer pair is tested, the confidence parameter is incremented as appropriate. The more variations detected, the higher the confidence value becomes. Such a method takes advantage of biological replicates to extract statistically significant changes in gene expression. Thus, these methods are largely unbiased by the fold change between the control and experimental groups. This circumvents the biases inherent to standard microarray analysis. Moreover, the methods described herein are superior to standard ANOVA techniques in their ability to qualify PCR dropouts without merging datasets.

In one embodiment, the methods are realized as software processes for performing GPR. More specifically, the methods are realized as Microsoft Excel-based software programs that output a ranked list of statistically changed genes using raw input data (cycle threshold—$C_T$ values) of up to five 96-well realtime PCR datasets from both a control and experimental group. The method compares the datasets from both groups using Excel's Students T-test after a multiple gene normalization. GPR thus enables a recognition of a change in gene expression pattern. In addition, GPR's output of ranked genes is not skewed by magnitude of expression change. Rather, GPR uses the power of biological replicates and the sensitivity of realtime PCR techniques to extract the most statistically changed genes, even if the expression fold change is small.

More broad embodiments are also possible. For example, the techniques may be applied to the analysis of medical images to assess disease progression and the effects of disease treatment. The techniques may also be applied to the analysis of biometric recognition studies (e.g., finger printing). Numerous other applications are possible, such as in the analysis of aerial and satellite photographs in general, and in the analysis of astro-photography in particular (e.g., to identify meteorites, comets, super novae, etc.).

In general, GPR may be used to analyze the change of any property in a subject. This may be done by furnishing an array depicting properties of the subject, performing an analysis with the array to collect a property dataset, filtering the property dataset to identify a set of normalizer properties, normalizing the property dataset using at least one property specific to the set of normalizer properties, and determining a ranking list using the normalized property dataset.

As contemplated by this application, an "array" may include any array depicting properties of a subject, for example, a gene or protein microarray, macroarry. Other exemplary embodiments also include an array of compounds, solutions, or other components of a subject. Pixel image arrays may also be used; other examples may include tissue arrays. Those skilled in the art will recognize that any array may be used.

A variety of techniques may be used to quantify and track changes in subjects, samples, etc. In certain embodiments, photo images are taken of a subject both before and after an event or period of time. Grayscale values may be assigned to individual pixels within each image. Optionally, blocks of pixels are formed and assigned grayscale values based on arithmetic average or, preferably, a geometric mean values of the individual pixels within the block. The GPR algorithm may be applied using the grayscale values of each image.

BRIEF DESCRIPTION OF THE DRAWINGS

The foregoing and other objects and advantages of the invention will be appreciated more fully from the following further description thereof, with reference to the accompanying drawings wherein;

FIG. 2 displays a data entry sheet used with one embodiment of the system;

DESCRIPTION OF ILLUSTRATED EMBODIMENTS

Figure 1:
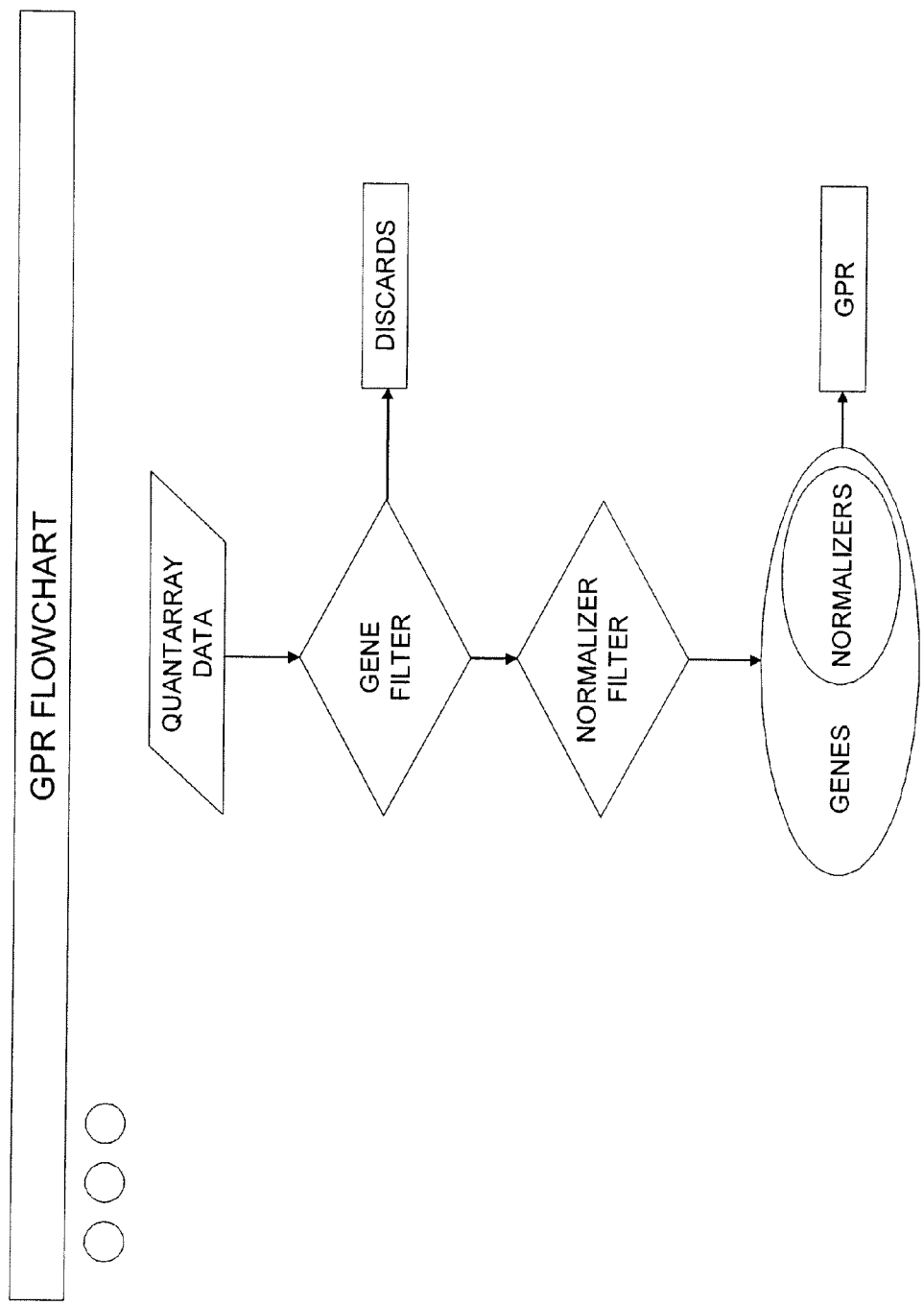
FIG. 1 depicts a flow chart diagram of one process according to the invention.

To provide an overall understanding of the invention, certain illustrative embodiments will now be described. For purpose of clarity, the invention will be described largely with reference to QPCR methods for analyzing large array of gene expression data. However, it will be understood by one of ordinary skill in the art that the systems and methods described herein can be adapted and modified for other suitable applications and that such other additions and modifications will not depart from the scope hereof. Such applications include, but are not limited to the analysis of microarrays, macroarrays, and protein arrays. For example, the systems and methods described herein have been adapted for performing microarray analysis of 25,000 genes or more. Other applications include the analysis of medical images to assess the level of disease progression and the effects of disease treatment. The techniques may also be used to analyze results from biometric recognition studies (e.g., finger printing). Those skilled in the art readily understand that numerous other applications are possible, such as the analysis of aerial and satellite photographs in general, and aspects of astro-photography in particular (e.g., to identify meteorites, comets, super novae, etc.).

PCR Applications

In certain embodiments, the techniques are used to analyze realtime PCR data or gene expression data. Traditional realtime PCR analysis involves normalization of a gene of interest to a 'housekeeping gene' such as 18S rRNA, GAPDH, HPRT, etc. A change in expression of a gene of interest could be gleaned by comparing the level of expression after normalization. There are two shortcomings to this approach. First, the choice of a normalizer gene is often arbitrary and is based on the assumption that the level of expression of the normalizer is invariant. Second, this method of expression analysis highlights genes that have large fold changes (up or down). While it is conceivable that in a biological situation, the most significant genes are the ones whose expression have changed dramatically, it is also possible that a small, reproducible change in other genes (e.g. transcription factors) may have substantial biological significance. This second shortcoming also applies to standard microarray techniques.

The multiple gene normalization described herein makes no pre-supposition about the constant level of expression of a particular normalizer. After filtering the data, GPR normalizes each eligible gene against every other gene that is eligible as a normalizer. Since GPR considers each gene individually, it is not as adversely affected by PCR dropouts as is ANOVA which merges data sets. Because it employs replicate sampling, GPR determines significance based on replicate consistency rather than by the magnitude of expression fold changes (the basis of microarray data analysis). Thus consistent small fold changes even in biologically important genes, such as transcription factors, expressed at low levels would be detected. Therefore, GPR overcomes the limitations of single gene normalization and is more flexible than ANOVA in the analysis of quantitative realtime RT-PCR data.

The systems and methods described herein analyze the results or expression experiments employing micro-titer and/or microarray plates and robotic plate readers. The system employs a set of self-normalizing housekeeping primers or, in other applications, oligonucleotides on the plates or arrays, depending on the application, and an algorithmic approach to normalizing expression data from all primers on the plate based on the reaction products of several of the self-normalizing gene primers or oligonucleotides. Normalization may be accomplished using simplex reactions involving these self-normalizing primers/oligonucleotides; the normalization parameters are then useable across all control and experimental reactions of the plate/array. A ranked list of genes whose amount of change is statistically significant can be determined. The accuracy of this list is enhanced by the data normalization aspect of the system.

Gene and Normalizers

Turning to FIG. 1, there is depicted a flow chart of one process wherein a quantarray of data is analyzed by a process that includes a gene filter step, a normalizer filter step, and the application of a pattern recognition process. More specifically, as shown in FIG. 1 and as explained in more detail below, the quantarray data is first processed by a gene filter. The gene filter sorts through the expression data and discards that portion of the expression data which seems to lack integrity and therefore may interfere with obtaining proper results. This may happen when a PCR process fails to take hold for some reason, and does not amplify the material. After the gene filter, the process proceeds to a normalizer filter. As discussed in more detail below, the normalizer filter will identify that set of expression data which relates to genes which may be used as normalizers. As depicted in FIG. 1 the resultant set of genes are understood to include data genes and normalizer genes that may be used for normalizing the collected expression data. The set of data genes and normalizer genes may be passed to the pattern recognition process which can identify those genes in the quantarray data which have varied in a statistically significant manner.

More particularly, the method can be understood from the following description of one exemplary process according to the invention for analyzing data collected by QPCR.

The process first filters data into overlapping gene and normalizer 'bins'. This filtering process is controlled by a user-defined Cycle Cutoff (CC) value. The CC is the PCR cycle number above which data is disregarded. After ~36-42 cycles, stochastic amplification of low copy-number targets can lead to large variability in the data. Consequently using the CC eliminates this noisy data. GPR's two filters employ the CC as described below.

Gene Filter: A gene passes through the 'gene filter' if, in one practice, all observations in either control and experimental groups fall below the cycle cutoff value. The following truth table describes output of the gene filter:

| ALL control data $\leq$ CC? | ALL experimental data $\leq$ CC | Output |
|---|---|---|
| True | True | True |
| False | True | True |
| True | False | True |
| False | False | False |

Thus, GPR will consider a gene for further analysis if it is well expressed in either control or experimental groups (or both), but will disregard a gene if it not well expressed ('off') in both groups.

Normalizer Filter: A gene passes through the 'normalizer filter' if, in one process, all observations in both control and experimental groups fall below the cycle cutoff value. The following truth table describes output of the normalizer filter:

| ALL control data $\leq$ CC? | ALL experimental data $\leq$ CC | Output |
|---|---|---|
| True | True | True |
| False | True | False |
| True | False | False |
| False | False | False |

Thus, GPR will consider a gene as a candidate normalizer on the conditions that it is well expressed in both control and experimental groups, but will disregard a gene if it not well expressed ('off') in either groups. This ensures that only genes that have measurable expression levels in both groups are used as normalizers and that genes that may be off (Ct>CC) are not considered as normalizers.

Figure 2:
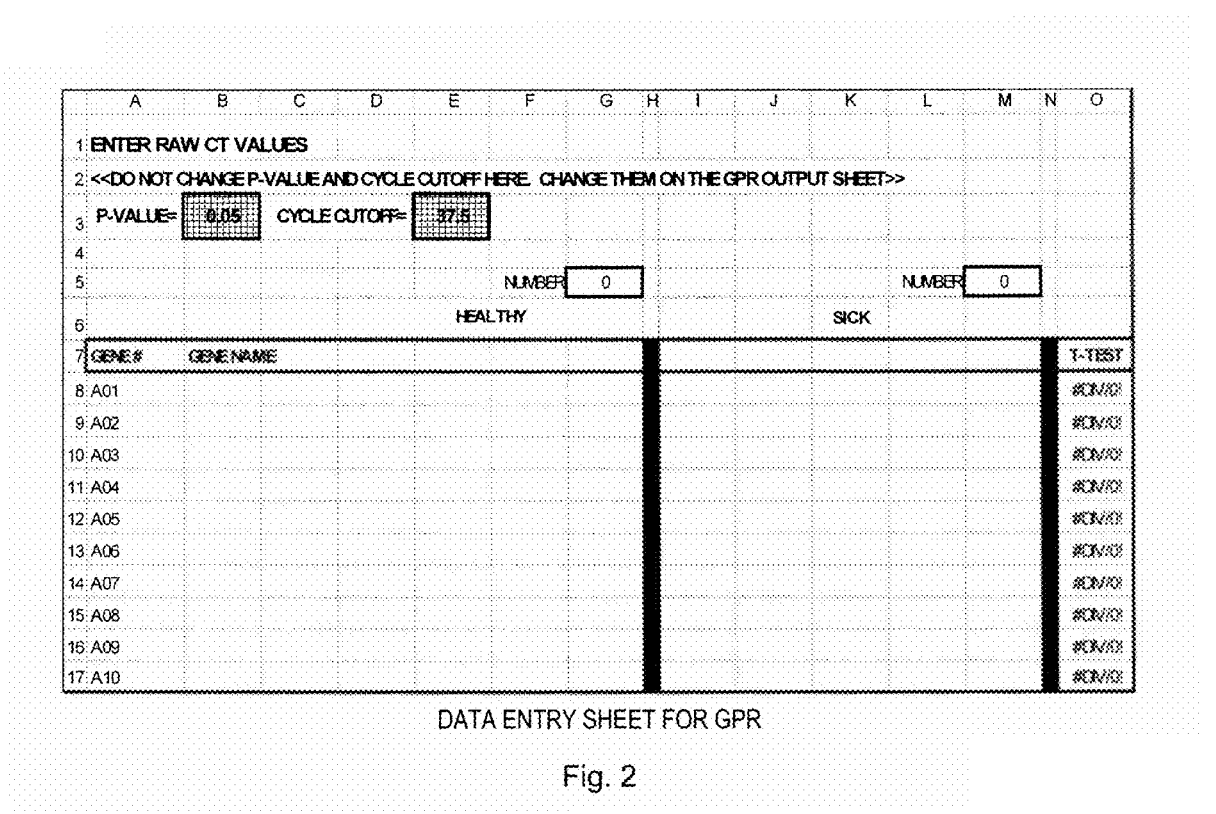

The list of genes that have passed either the gene or the normalizer filters is shown in FIG. 2 in the box to the right of the input area on the 'Raw Ct Values' sheet.

Global Pattern Recognition

After applying the gene and normalizer filters, GPR then proceeds with global pattern recognition.

Figure 4:
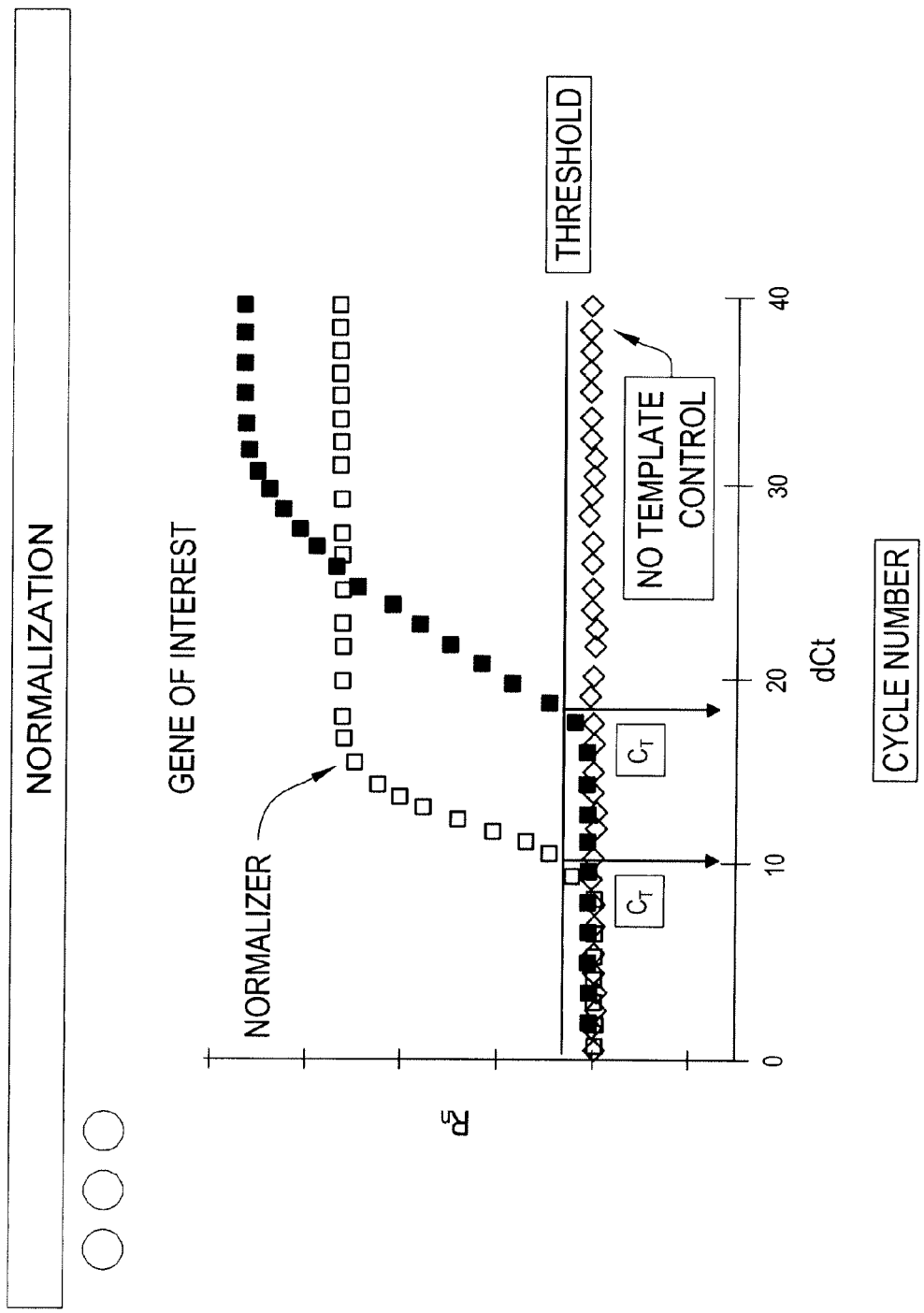
FIG. 4 depicts a gene normalization process.
Figure 5:
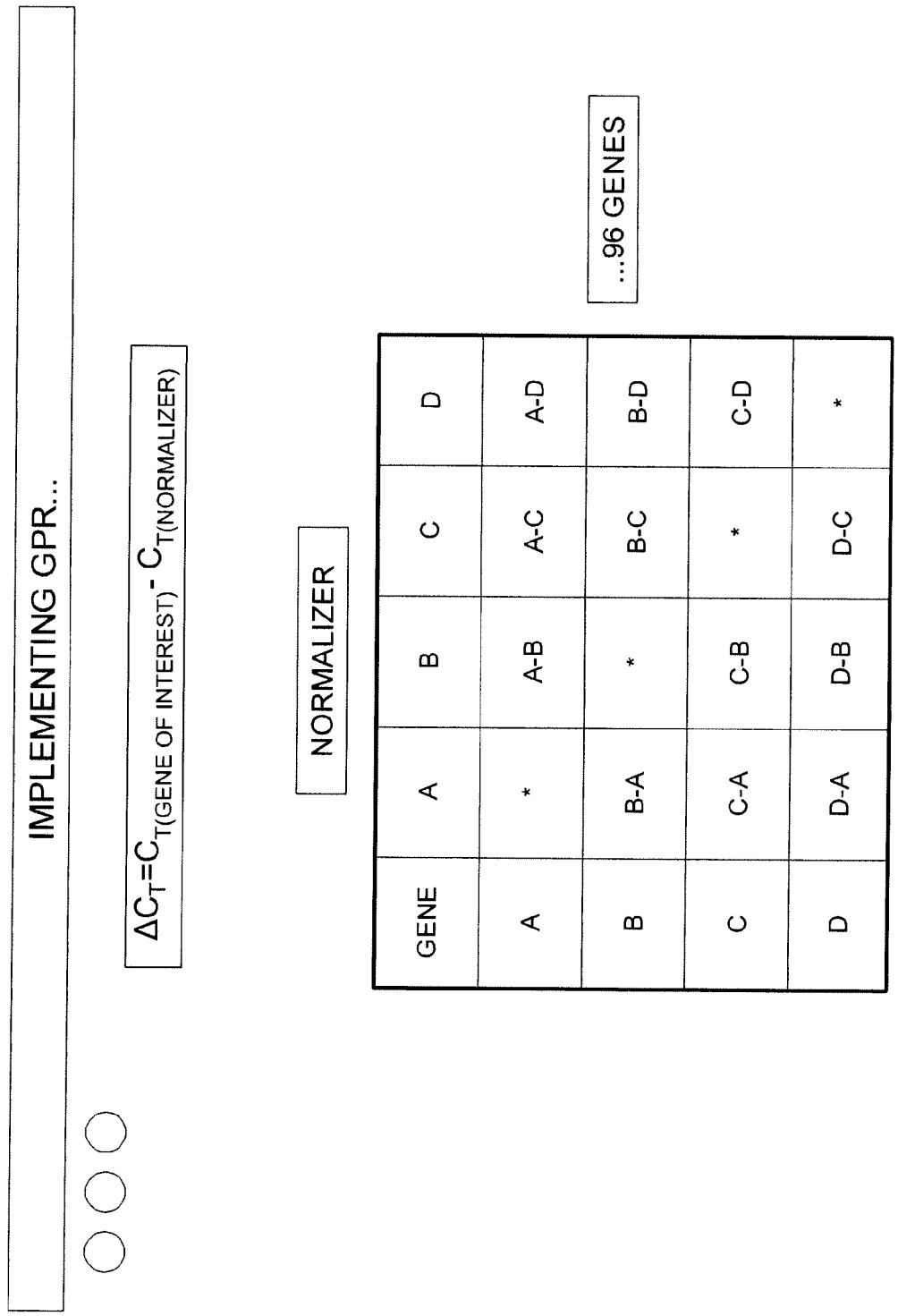
FIG. 5 depicts a normalization process for 96 genes.

In one practice, for each dataset (column of 96 Ct values), GPR takes each eligible gene and normalizes it to each eligible normalizer in succession to generate a $\Delta C_T$ values as follows: $\Delta C_{T\,Gene} = C_{T\,Gene} - C_{T\,Normalizer}$. This normalization process is depicted graphically in FIG. 4. Specifically, FIG. 4 shows the relative florescence of a normalizer gene as well as the gene of interest. More specifically, FIG. 4 shows a graph wherein the cycle numbers are set out along the X-axis and the relative florescences set out along the Y-axis. The normalizer gene and the gene of interest are shown as plots on these graphs and a cycle threshold line is presented. The difference between cutoff thresholds is shown in FIG. 4 by dCt and in FIG. 4 this is approximately 8 cycles difference. As shown in FIG. 5 the $\Delta C_T$ values for each gene of interest may be generated. For each gene-normalizer combination, the $\Delta C_T$ values generated for the control and experimental groups are compared by a two-tailed heteroscedastic (unpaired) Student's T-test and a 'hit' is recorded if the p-value from the T-test falls below a user-defined p-value (e.g. 0.05).

Figure 6:
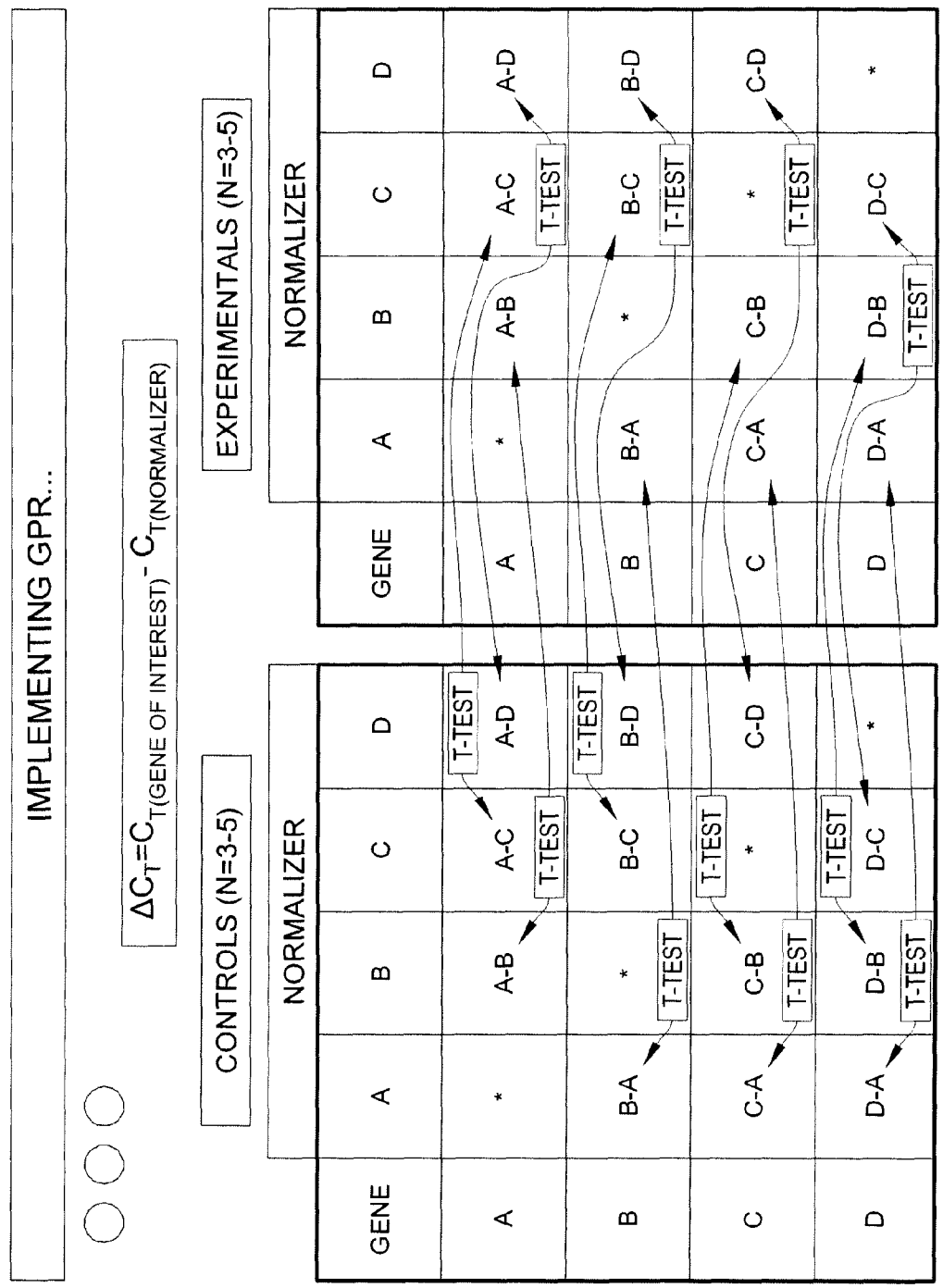
FIG. 6 depicts a pattern detection process.

The process for implementing the pattern recognition analysis is depicted graphically in FIG. 6. Specifically, FIG. 6 illustrates that for each gene-normalizer combination the $\Delta C_T$ values generated for the control and experimental groups may be compared. In the embodiment depicted by FIG. 6 each of these combinations is compared by the T-test. The T-test allows the researcher to make a hypothesis as to what a statistically significant variation would be between the control data and the experimental data. In this way, the comparisons being made may determine which of the gene-normalizer combinations appear to have varied in a statistically significant manner. Other statistical analysis may be used, although the T-test has the benefit of being well known and incorporated in Microsoft Excel.

Figure 7:
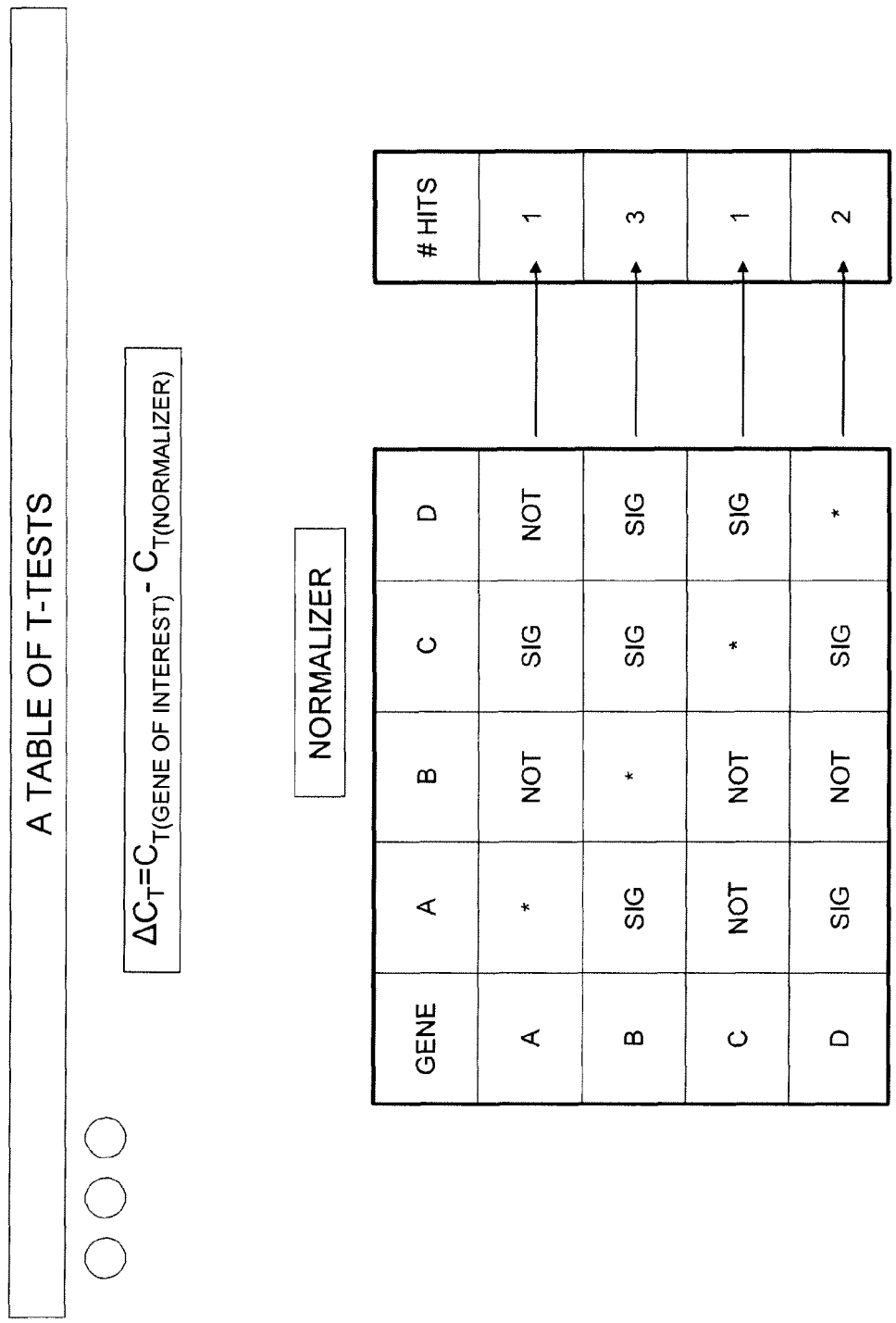
FIG. 7 depicts a pattern recognition process.

As discussed above, each time a significant variation is detected, a hit may be recorded for that gene. This is depicted graphically in FIG. 7 which shows the gene-normalizer combinations earlier presented in FIG. 6. At each gene normalizer combination an indication may be recorded as to whether the T-test indicated a statistically significant variation between experimental data and control data. For each gene, the number of hits identified can be added and recorded. This is shown in FIG. 7 by the "# hits" column. In this case, the gene A records only one significant hit. That hit occurred for the gene normalizer combination A-C. In contrast, the gene B records three significant hits for the gene normalizer combinations B-A, B-C, and B-D.

At the end of the normalization routine, GPR, in one practice, tallies the hits for each gene against all eligible normalizers and ranks the genes in descending order of number of hits. An experiment-independent score is obtained by dividing the number of hits for a gene by the total number of eligible normalizers (e.g. 50 hits out of 65 eligible normalizers is a score of 0.769). The genes with the highest scores have changed most significantly in the dataset. Genes that failed to pass through the gene filter are assigned −1 hits and a "N.S." (not significant) in the score column and are ranked alphabetically at the bottom of the output page (increasing the CC usually makes more of these genes 'significant').

To obtain a sense for the direction and magnitude of the change, the fold change of each gene (average change in experimental group vis-à-vis the control group) is also computed by the $\Delta\Delta C_T$ method using 18S rRNA expression level as a normalizer. Upregulated genes are shown in red and downregulated genes are indicated in green. Additionally numerical fold change is preceded by a minus (−) sign for a downregulated gene. We note that if 18S rRNA expression is a PCR dropout, GPR is unaffected, but fold change computations for that biological replicate may throw off the average fold change output on the GPR output page. Consider either removing the entire column of $C_T$ values for that replicate or imputing the value of 18S rRNA CT from the other replicates in the group.

FIG. 2 (below) displays the data entry sheet of one embodiment of GPR, which is available for download upon request at the Jackson Lab website. The sheet is titled 'Raw Ct values'. The technique is applied as follows:

Enter gene names for the targets in the 'Gene Name' column. Enter up to 96 $C_T$ values for up to five biological replicates in the two comparison groups. The control group is designated as 'Healthy' and the experimental group is designated as 'Sick'. Do not change any of the other parameters on this sheet (including the 'Pre-output' and 'H12 (18S)' sheets, or else the analysis may be compromised.

After entering CT values and gene names switch to the 'GPR Output' sheet by clicking on the tabs at the bottom of the Microsoft Excel spreadsheet. You will see the sheet as shown in FIG. 3.

1. Enter the name of your experiment in cell below the GPR title (FIG. 3 shows 'KRN RA: 8 week bloods).
2. Enter the desired p-value for significance cutoff (for the T-test of $\Delta C_T$ values) and the Cycle Cutoff in the cells below the experiment title line.
3. Hit the 'Sort' button in the upper right of the sheet (framed by a red box).
4. Alternately, enter the desired Cycle Cutoff and then hit one of the preset p-values buttons (below the 'Sort' button) to automatically set the p-value and sort the list.
5. The page has been setup to print the entire GPR output sheet onto one page.

Brief Description of GPR's Output

Figure 3:
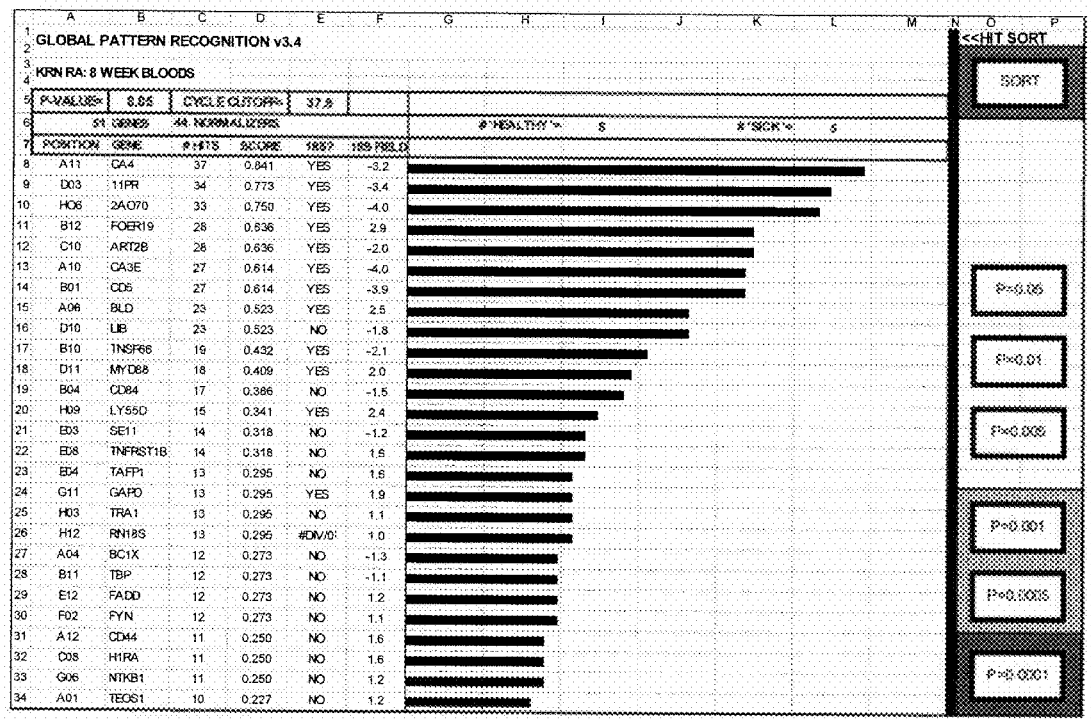
FIG. 3 depicts an example output page.

As shown in FIG. 3, the GPR output page contains a lot of summary data regarding the input datasets. The number of eligible genes and normalizers that have passed the respective filters are listed below the p-value/Cycle Cutoff line. Also listed is the number of healthy (control) animals and sick (experimental) animals in the data set. This is computed from the number of entries in position A01 of the GPR entry field (on the 'Raw Ct values' sheet). Genes are ranked in descending order of the number of normalizer hits they obtain. The score is computed by dividing the number of hits by the number of eligible normalizers. The '18S?' column describes if the gene is significant after normalization to 18S rRNA (by a T-test of the $\Delta C_T$ values). This column is included to gain a sense for the quality of the data. The '18S Fold' column describes the average fold change for the gene compared to 18S rRNA expression. To choose a different normalizer for fold change analyses, simply place the normalizer gene's expression data in position H12 and change the appropriate title cells on the GPR Output sheet. The red background describes genes that are upregulated and the green background—genes that are downregulated. Blue thermometers to the right of the '18S Fold' column provide a graphical representation of the score.

Experimental Design for GPR

Since GPR takes advantage of biological replicates, meaningful data is obtained with the following experimental design. An entire plate of 96 genes is run for each biological replicate (usually 3 controls and 3 experimentals—GPR can handle up to 5 controls and 5 experimentals). It is possible to run fewer than 96 genes per biological replicate (e.g. 48 genes per animal, such that two samples can be fit onto one plate) and this will be described in a later section. The raw $C_T$ values for each replicate are then entered and analyzed by GPR. Thus for 6 animals (3 in each group) run against 96 genes, 6 runs will have to be run on the 7000/7700 (96-well format). Our recommendation is for a minimum of 4 animals in both comparison groups with 5 being optimal. Appendix A provides one list of 96 genes used for one experiment as described herein. This list include plate position, full gene name, gene symbol and genbank accession number.

In one embodiment the plate comprises a one piece, injection-moulded PCR plate in the industry standard 96-well format, providing handling convenience and compatibility with high throughput automated systems. Alternatives may be employed including, but not being limited to polycarbonate plates, and plates of other sizes. The plates may be high profile or low profile, skirted or semi-skirted and the type of plate employed will depend upon the application at hand. In those practices, described in more detail below, where the GPR techniques described herein are applied to micro array, macro array or other array type datasets, the process may substitute arrays for plates.

Analyzing Fewer than 96 Genes with GPR

Analyzing fewer than 96 genes per biological replicate is possible with GPR. To facilitate sample handling it is convenient to have a multiple of 24 genes per biological replicate (e.g. 24, 48, 96). Results show that a minimum of 48 genes (with at least half of them remaining relatively unchanged between the two comparison groups) provides the most reliable data. If 24 genes are being analyzed, at least half of these should be normalizers.

Once the data is obtained, it can be entered into GPR. Since GPR is designed to handle 96 $C_T$ values, when entering fewer data points, the following considerations should be taken:

1. Enter genes and gene names at the top of the entry fields of GPR.
2. Enter 40 as a $C_T$ value for all unused gene positions.
3. Enter the $C_T$ values for the normalizer against which you wish to compute fold changes at position H12 (at the bottom of the list). We use 18S rRNA for our relative fold change computations.

Data can then be analyzed with GPR. Unused gene positions appear at the bottom of the ranked list.

Handling PCR Dropouts with GPR

Occasionally users may observe apparent PCR dropouts (or linear creepers—A non-exponential PCR) in their dataset. It is left to the user's discretion to decide what is a true dropout versus actual variability in gene expression. If a particular data point is considered a true dropout simply leave the cell empty in the GPR entry page. For example, for β-actin expression, the $C_T$ values obtained for one group may be 24, 23.9, 22.7, 39.4 and 25.1. The 39.4 $C_T$ value appears to be an obvious dropout considering the nature of the gene (β-actin—a classic normalizer). In this case, leaving the other values alone, simply leave the cell empty in place of the 39.4 value. It is important to check the quality of the other genes' $C_T$ values from that biological replicate to see if they are similarly affected. In such a case, that entire sample may have to be disregarded as a procedural error.

384GPR and 1536GPR

To analyze data generated with the 384 gene ABI 7900 and a possible 1536 gene instrument, 384GPR and 1536GPR were created. These versions of GPR differ in three ways from the 96 gene version:

The algorithm is the same as that used in the 96 gene version of GPR however rather than calculating all delta $C_T$ values at one time (which would be impractical within Excel's limitations), 384GPR and 1536GPR calculate delta $C_T$ values dynamically, one at a time. Consequently, they take longer to implement, but give similar results to the 96 gene version of GPR.

Due to size limitations, the output is simply a ranked list of normalizer hits and corresponding gene scores (including information about the number of control and experimental animals, number of genes and normalizers, the p-value and Cycle Cutoff).

It is not necessary to fill in unused $C_T$ positions with "40" since the program will automatically ignore unused rows. However, there should be no empty rows in between data rows or else the program will only consider data rows before the first empty row. Consequently ensure that all the data rows are above the first empty row.

ArrayGPR

While originally designed to analyze QPCR data, the GPR algorithm can also be used to analyze single or two-color microarray data. To do so, ArrayGPR, a program capable of analyzing up to 25,000 genes was created. Similar to 384GPR and 1536GPR, ArrayGPR calculates the microarray equivalent of delta $C_T$ values dynamically.

However, to handle microarray data in the GPR algorithm, the fluorescence intensity values generated from microarrays are first converted from linear values to logarithmic values (to resemble the logarithmic output of QPCR data). In addition, since higher values in microarray data denote higher amounts of gene expression while in QPCR, higher $C_T$ values denote lower amounts of gene expression, the values obtained from the log transform are multiplied by −1. The p-value behaves as before, however the user enters a value for the intensity cutoff (analogous to the Cycle Cutoff for QPCR/GPR). This value is also entered as a linear value, e.g. 150, which is converted by the program using a negative log transform. The transformed intensity cutoff is used exactly as the Cycle Cutoff was used to affect the gene and normalizer filters.

ArrayGPR will rank genes according to statistical significance, regardless of the magnitude of the change. Similar to the GPR programs for QPCR, the data must be in the format of a column of values for each of the controls and the experimentals. This holds whether the data for each sample was obtained in a single color or from a two color experiment.

Thus, ArrayGPR provides a useful alternative to the myriad approaches to "normalize" array data. In addition, since in any experimental manipulation, the level of expression of the vast majority of genes remains unchanged, ArrayGPR takes advantage of a huge number of normalizer genes to obtain a true global pattern of gene expression.

The GPR algorithm may also be applied to the analysis of "macroarrays" (e.g. Atlas™ blots) and to future protein arrays, and in reality to any array of genes analyzed across groups of (unpooled) control and experimental samples. In these cases, the data is linear and densitometric in nature. These data can be analyzed after the negative log transform function of ArrayGPR. Of course, the intensity cutoff values will have to be adjusted to account for differences in dynamic range among the various techniques, though the principle remains true. As for all GPR applications, samples should not be pooled and should be analyzed individually as controls and experimentals.

Further Applications of GPR

Those skilled in the art recognize that the methods disclosed herein are applicable to a wide variety of scientific problems. In general, GPR may be used for recognition of patterns and identification of differences in any datasets which include replicate images acquired before and after an event, alteration of conditions or other change. The GPR concept is based on statistical comparisons among the replicate images. This provides a statistical basis for damping out image variability and noise, thus revealing changes that are most probably related to quantum events. Since this damping is performed computationally, it substantially reduces the bias and time-consuming need for human interpretation early in the analytic process. Changes that pass a specified cutoff can be flagged for inspection by an experienced technician.

Datasets derived from any source or process may be analyzed according to the methods. For example, certain applications extend to the use of photographic images to study changes in biological processes as shown, for example, by changes in a pixel dataset. In such embodiments, pixels in a photograph may be monitored over time to track changes in a property of interest (e.g., color, shading, image size) as depicted within each pixel. Datasets may be formed with pixels derived over time (e.g., before and after an event). Pixel data (for example, data showing changes in pixels of interest such as changes in the size of certain images within the pixels of interest) may then be normalized to corresponding changes in other pixels (i.e., the normalization pixels). Statistical analyses similar to those described herein may be applied to assess changes in certain observed properties within pixels, and charts analogous to FIGS. 2 and 3 and others described herein may be prepared to assist in the analysis of the changes occurring in the underlying processes.

In certain embodiments, at least one image containing a specific landmark location may be analyzed (analogous to a gene position in GPR) and used as GPR input data. In certain embodiments, the image is analyzed at the level of at least one pixel or pixel block, each having a grayscale value that is used as GPR input data (analogous to microarray data, this input is linear in nature and would undergo a negative log transform prior to GPR analysis). The number of shades of gray of an image may be increased or decreased as desired. Other pixels may also be selected and, in certain embodiments, more than one pixel may be collated and assigned as a referent pixel block. A grayscale value may be assigned to the referent pixel block. Subsequent images may be taken, for example after an event of interest, that also include the landmark location and other landmarks identified in the referent pixel or pixel block.

A pixel block may be any size, for example 10×10 pixels square (or much smaller (e.g., 2×4), or even much larger (e.g., 100×100)). The size of the block may be increased or decreased as desired. An arithmetic average or, preferably, a geometric mean may be calculated from grayscale values of the pixels within a block, and such value may be used as a data point for GPR analysis. An analogous value may be applied to each desired block within the image. The grayscale values (linear measures) are converted to logarithmic values by a negative log transformation.

In certain embodiments, images are taken of a subject both before and after a period of time, for example before and after an event of interest. Individual pixels or pixel blocks within each image are assigned gray scale values and analyzed to identify pixels or pixel blocks that have changed after the event of interest. The GPR analysis, including its filtering and normalizing steps, is applied to the images as described above.

In certain embodiments, the methods may be applied to the analysis of medical images to assess the level of disease progression and the effects of disease treatment. The applications include the use of the GPR algorithm to analyze changes in tissues, organs, and other physiological components as may be viewed by X-ray, CAT scan, photographs or any other medical imaging devices or modalities.

Replicate images obtained prior to treatment (e.g. surgery or chemotherapy for a tumor) may be compared to images obtained during or after treatment to highlight changes. GPR analysis is not only able to highlight changes in tumor size but collateral damage, new metastases, and other changes that might arise in the same image that may not be the subject of a technician's direct investigation. Additionally, CT and MRI scanners are able to collect data that is beyond the capacity of the human eye to perceive (i.e. far more shades of gray than can be perceived by the human eye), thus quantification of the grayscale values and GPR analysis will allow the quantification of treatment effect (for example, through a GPR score) which is unbiased.

For example, to assess whether a tumor has metastasized to the lungs, three Positron Emission Tomography (PET) images of a patient's thorax are taken in January. Three replicate images are then taken in April. The images are overlayed and single or blocks of grayscale pixels are subjected to the GPR algorithm, resulting in a ranked list based on the significance of the change. The GPR scores are then converted to a color scale and mapped back to the original image coordinates. The experienced technician may then use the color scaling to identify image features highlighted by high GPR values. In this way, discrete image changes, such as the appearance of a small metastatic nodule, can be flagged and identified.

The methods are also useful for analyzing changes in concentration of certain biochemical components as a result of disease progression or treatment protocols. The techniques may also be applied to the analysis of biometric recognition studies (e.g., finger printing). Any data gathered with respect to changes in biochemical conditions (e.g., changes in plasma, tissue, or cellular concentration of biochemical or other components) may be analyzed using the methods described herein.

In still other embodiments, the techniques are applicable to the analysis of aerial and satellite photographs. For example, the methods described herein may be adapted to identify changes in planetary systems (e.g., to identify meteorites, comets, super novae, etc.), or even to study changes in surface properties of planets and other systems. In certain embodiments, replicate images are compared to highlight changes in a geographic space (e.g. erecting new buildings or tents, populating an area with troops and equipment, etc.). Gradual image changes, such as the assembly of a permanent structure, can be monitored by comparing replicate images over a wide time period. For example, three images may be taken in a week in January and compared to three images taken of the same subject space in a week in March. Image change over any period of time may be monitored. For example, rapid image changes, such as the deployment of troops to a new camp, may be monitored by comparing replicate images taken over a short period (for example images from three consecutive days with images from the next three consecutive days).

The same methodology is applicable to the rapid assessment of natural disasters. Other applicable changes may include changes in an ecosystem over time (e.g., by erosion, natural disaster, pollution), or even including military uses such as bomb damage assessments. For example, replicate images obtained prior to a bombing run can be compared to post-mission images to quickly highlight areas of damage (in a quantifiable manner with GPR a score). This type of analysis may also highlight areas of collateral damage.

In other embodiments, the methods are applied to the analysis of personal identification. Replicate past identification photos can be compared to current photos to assess areas of change, and areas that have not changed. For example, photographs of suspect faces taken in the past may be compared by the methods with more recent photographs to identify the subject. In certain embodiments, the lower the GPR score, the more likely the measured feature (e.g., a facial feature) has remained unchanged. This might be applied to identifying people before and after plastic/reconstructive surgery or in a more developed form for post-mortem identification with ante-mortem photographs.

In certain embodiments, GPR is employed to analyze disease progression in a subject, comprising furnishing an array of pixels taken from a medical image depicting properties of the subject; performing an analysis with the array to collect a property dataset; filtering the property dataset to identify a set of normalizer pixels; normalizing the property dataset using properties specific to the set of normalizer pixels; and determining a ranking list using the normalized property dataset.

In certain embodiments, an array is furnished analogously to the arrays described above, which may include providing a plurality of arrays having at least one control property. In certain embodiments, furnishing an array includes providing a plurality of arrays having at least one property of any type, including properties indicating the presence of a disease in a subject. Furnishing an array may also include forming a plurality of data points charting properties in control samples and experimental samples.

In certain embodiments, employing GPR includes measuring, for each pixel in an array, a parameter associated with a property representative of a threshold parameter. In certain embodiments filtering includes analyzing the property dataset to sort pixels into categories of normalizer pixels and data pixels. Filtering may also include removing from a property dataset pixels that depict a property that does not meet a specified threshold parameter.

In certain embodiments, normalizing a property dataset includes determining for a pixel differences in properties included in the respective pixel and in pixels in the identified set of normalizing pixels. The normalizing process compares each pixel or pixel block in a data set to determine differences in properties between each pixel, pixel block, etc., and the pixel or pixels identified in the set of normalizing pixels.

As noted, a ranking list of properties of interest may be developed by identifying a pattern of variance between properties shown in pixels associated with an experimental sample and corresponding properties shown in pixels associated with a control sample.

In certain embodiments, processing normalized data includes quantifying a pattern of variance between properties in a control group and properties in an experimental group and ranking properties as a function of the quantified pattern of variance. It may also include performing a T-test or other statistical analysis to identify a measure of similarity between a property in an experimental group and a property in a control group.

The methods also include tallying for a test pixel a score representative of a number of normalizer pixels depicting a statistically relevant variation in a property of interest.

The methods described herein can be operated on conventional data processing platforms such as an IBM PC-compatible computer running the Windows operating systems, or a SUN workstation running a Unix operating system. Alternatively, the data processing system can comprise a dedicated processing system that includes an embedded programmable data processing system that can include the GPR process described. For example, the data processing system can comprise a single board computer system that has been integrated into a system for performing microarray analysis. The single board computer (SBC) system can be any suitable SBC, including the SBCs sold by the Micro/Sys Company, which include microprocessors, data memory and program memory, as well as expandable bus configurations and an on-board operating system.

As discussed above, the GPR systems and methods can be realized as a software component operating on a conventional data processing system such as a Unix workstation. In that embodiment, the GPR system can be implemented as a C language computer program, or a computer program written in any high level language including C++, Fortran, Java or basic. Additionally, in an embodiment where microcontrollers or DSPs are employed, the GPR system can be realized as a computer program written in microcode or written in a high level language and compiled down to microcode that can be executed on the platform employed. The development of such systems is known to those of skill in the art, and such techniques are set forth in Digital Signal Processing Applications with the TMS320 Family, Volumes I, II, and III, Texas Instruments (1990). Additionally, general techniques for high level programming are known, and set forth in, for example, Stephen G. Kochan, *Programming in C*, Hayden Publishing (1983). It is noted that DSPs are particularly suited for implementing signal processing functions, including preprocessing functions such as image enhancement through adjustments in contrast, edge definition and brightness. Developing code for the DSP and microcontroller systems follows from principles well known in the art.

Those skilled in the art will know or be able to ascertain using no more than routine experimentation, many equivalents to the embodiments and practices described herein. Accordingly, it will be understood that the invention is not to be limited to the embodiments disclosed herein, but is to be understood from the following claims, which are to be interpreted as broadly as allowed under the law. All references identified herein are hereby incorporated by reference in their entireties.

TABLE 1

Genes included in the ImmunoQuantArray.

| Position | Gene | Genbank Acc | Name |
| --- | --- | --- | --- |
| A1 | Icosl | AF216747 | ICOS-ligand |
| A2 | Bad | NM_007522 | Bcl-associated death promoter |
| A3 | Bax | NM_007527 | Bcl2-associated X protein |
| A4 | Bcl2 | NM_009741 | B-cell leukemia/lymphoma 2 |
| A5 | Bcl2l | NM_009743 | Bcl2-like [Bcl-x] |
| A6 | Bid | U75506 | BH3 interacting domain death agonist |
| A7 | Cd1d1 | M63695 | CD1d1 antigen |
| A8 | Cd28 | NM_007642 | CD28 antigen |
| A9 | Cd34 | S69293 | CD34 antigen |
| A10 | Cd3e | M23376 | CD3 antigen, epsilon polypeptide |
| A11 | Cd4 | NM_013488 | CD4 antigen |
| A12 | Cd44 | M27130 | CD44 antigen |
| B1 | Cd5 | NM_007650 | CD5 antigen |
| B2 | Cd80 | AF065894 | CD80 antigen |
| B3 | Cd86 | NM_019388 | CD86 antigen |
| B4 | CD8a | AJ131778 | CD8 antigen, alpha chain |
| B5 | Cd8b | NM_009858 | CD8 antigen, beta chain |
| B6 | Csf1 | NM_007778 | Colony stimulating factor 1 (macrophage) |
| B7 | Csf3 | NM_009971 | Colony stimulating factor 3 (granulocyte) |
| B8 | Csk | NM_007783 | C-src tyrosine kinase |
| B9 | Tnfrsf6 | NM_007987 | Tumor necrosis factor receptor superfamily, member 6 [Fas] |
| B10 | Tnfsf6 | NM_010177 | Tumor necrosis factor (ligand) superfamily, member 6 [FasL] |
| B11 | Fcer1a | NM_010184 | Fc receptor, IgE, high affinity I, alpha polypeptide |
| B12 | Fcer1g | NM_010185 | Fc receptor, IgE, high affinity I, gamma polypeptide |
| C1 | Fcgrt | NM_010189 | Fc receptor, IgG, alpha chain transporter |
| C2 | Hcph | NM_013545 | Hemopoietic cell phosphatase |
| C3 | Ifnb | NM_010510 | Interferon beta, fibroblast |
| C4 | Ifng | M28621 | Interferon gamma |
| C5 | Il12a | NM_008351 | Interleukin-12 [p35 subunit] |
| C6 | Il12b | NM_008352 | Interleukin-12 [p40 subunit] |
| C7 | Il18 | NM_008360 | Interleukin 18 |
| C8 | Il10ra | NM_008348 | Interleukin 10 receptor, alpha |
| C9 | Il12rb2 | NM_008354 | Interleukin 12 receptor, beta 2 |
| C10 | Il1r1 | NM_008362 | Interleukin 1 receptor, type I |
| C11 | Ilrak | NM_008363 | Interleukin 1 receptor-associated kinase |
| C12 | Il2ra | NM_008367 | Interleukin 2 receptor, alpha chain |
| D1 | Il2rg | NM_013563 | Interleukin 2 receptor, gamma chain |
| D2 | Il4ra | NM_010557 | Interleukin 4 receptor, alpha |
| D3 | Il7r | NM_008372 | Interleukin 7 receptor |
| D4 | Itgal | AF065901 | Integrin alpha L |

TABLE 1-continued

Genes included in the ImmunoQuantArray.

| Position | Gene | Genbank Acc | Name |
| --- | --- | --- | --- |
| D5 | Itgam | NM_008401 | Integrin alpha M |
| D6 | Lck | M12056 | Lymphocyte protein tyrosine kinase |
| D7 | Ltbr | NM_010736 | Lymphotoxin B receptor |
| D8 | Zfp106 | AF060246 | Zinc finger protein 106 |
| D9 | Lta | NM_010735 | Lymphotoxin A |
| D10 | Ltb | NM_008518 | Lymphotoxin B |
| D11 | Myd88 | NM_010851 | Myeloid differentiation primary response gene 88 |
| D12 | Nos2 | NM_010927 | Nitric oxide synthase 2, inducible, macrophage |
| E1 | Pfp | M23182 | Pore forming protein [Perforin] |
| E2 | Ptprc | NM_011210 | Protein tyrosine phosphatase, receptor type, C |
| E3 | Sell | NM_011346 | Selectin, lymphocyte |
| E4 | Tgfb1 | AJ009862 | Transforming growth factor, beta 1 |
| E5 | Tlr2 | AF185189 | Toll-like receptor 2 |
| E6 | Tlr4 | AF185285 | Toll-like receptor 4 |
| E7 | Tnfrsf1a | NM_011609 | Tumor necrosis factor receptor superfamily, member 1a |
| E8 | Tnfrsf1b | NM_011610 | Tumor necrosis factor receptor superfamily, member 1b |
| E9 | Btk | NM_013482 | Bruton agammaglobulinemia tyrosine kinase |
| E10 | C2ta | NM_007575 | Class II transactivator |
| E11 | Ccxcr1 | NM_011798 | Chemokine (C motif) XC receptor 1 |
| E12 | Fadd | NM_010175 | Fas-associated via death domain |
| F1 | Cflar | U97076 | CASP8 and FADD-like apoptosis regulator [FLIP(L)] |
| F2 | Fyn | NM_008054 | Fyn proto-oncogene |
| F3 | Hsp70-2 | NM_008301 | Heat shock protein, 70 kDa 2 |
| F4 | Hsp70-1 | M35021 | Heat shock protein, 70 kDa 1 |
| F5 | Il10 | NM_010548 | Interleukin 10 |
| F6 | Il15 | NM_008357 | Interleukin 15 |
| F7 | Il1b | NM_008361 | Interleukin 1 beta |
| F8 | Il2 | NM_008366 | Interleukin 2 |
| F9 | Il4 | NM_021283 | Interleukin 4 |
| F10 | Il5 | NM_010558 | Interleukin 5 |
| F11 | Il6 | M20572 | Interleukin 6 |
| F12 | Il7 | NM_008371 | Interleukin 7 |
| G1 | Jun | NM_010591 | Jun oncogene |
| G2 | Lcp2 | NM_010696 | Lymphocyte cytosolic protein 2 |
| G3 | Scyc1 | U15607 | Small inducible cytokine subfamily C, member 1 [Lymphotactin] |
| G4 | Map2k1 | NM_008927 | Mitogen activated protein kinase kinase 1 [MEK1] |
| G5 | Map2k2 | NM_023138 | Mitogen activated protein kinase kinase 2 [MEK2] |
| G6 | Nfkb1 | NM_008689 | Nuclear factor of kappa light chain gene enhancer in B-cells 1, p105 |
| G7 | Rag1 | NM_009019 | Recombination activating gene 1 |
| G8 | Scya19 | AF307988 | Small inducible cytokine A19 |
| G9 | Scya20 | NM_016960 | Small inducible cytokine subfamily A20 |
| G10 | Ifng | K00083 | Interferon gamma |
| G11 | Scyd1 | NM_009142 | Small inducible cytokine subfamily D, 1 |
| G12 | Terc | AF047387 | Telomerase RNA component |
| H1 | Tert | NM_009354 | Telomerase reverse transcriptase |
| H2 | Tnf | X02611 | Tumour necrosis factor |
| H3 | Tra1 | NM_011631 | Tumor rejection antigen gp96 |
| H4 | Tnfsf11 | AF013170 | Tumor necrosis factor (ligand) superfamily, member 11 |
| H5 | Tnfrsf11b | NM_008764 | Tumor necrosis factor receptor superfamily, member 11b (osteoprotegerin |
| H6 | Zap70 | NM_009539 | Zeta-chain (TCR) associated protein kinase (70 kD) |
| H7 | Ifna1 | NM_010502 | Interferon alpha family, gene 1 |
| H8 | Cd3z | U17267 | T cell receptor-zeta chain |
| H9 | Kirb1d | AF338322 | Killer cell lectin-like receptor subfamily B member 1D |
| H10 | Itgax | NM_021334 | Integrin alpha X |
| H11 | Mox2 | AF231126 | Antigen identified by monoclonal antibody MRC OX-2 |
| H12 | Rn18s | X00686 | 18S RNA [ribosomal] |

We claim:

1. A method for comparing gene expression data between a control sample and an experimental sample, comprising (a) furnishing a control array and an experimental array, wherein the control and experimental arrays have a common set of primers for detecting a set of genes of interest;

(b) performing real-time polymerase chain reaction (RT-PCR) analysis for the control sample using the control array to generate a control expression dataset, (c) performing RT-PCR analysis for the experimental sample using the experimental array to generate an experimental expression dataset, (d) filtering each of the control and experimental datasets to identify, based on the RT-PCR data, a set of data genes and a set of normalizer genes, wherein (i) the set of data genes is a subset of the set of genes of interest, the set of data genes comprising genes that have data values below a predetermined threshold in either the control dataset or the experimental dataset, and (ii) the set of normalizer genes is a subset of the set of data genes, the set of normalizers genes comprising genes that have data values below a predetermined threshold in both the control dataset and the experimental dataset;

(e) normalizing each of the control and experimental datasets, comprising:
  (i) comparing expression data for each data gene in the control dataset with expression data for each normalizer gene in the control dataset to identify a control difference value for each data gene-normalizer gene pair of the control dataset;
  (ii) comparing expression data for each data gene in the experimental dataset with expression data for each normalizer gene in the experimental dataset to identify an experimental difference value for each data gene-normalizer gene pair of the experimental dataset;
(f) comparing the control difference value of a data gene-normalizer gene pair with the experimental difference value of the corresponding data gene-normalizer gene pair, wherein a change in the difference value indicates that the expression levels of the data gene may be different in the control sample as compared to the expression level of the same data gene in the experimental sample;
(g) ranking the set of data genes based on the comparisons of difference values in step (f); and
(h) outputting at least one of the ranked list and information based on the ranked list in a user readable format.

2. A method according to claim 1, further comprising performing two or more replicate RT-PCR analyses for the control sample to generate the control dataset.

3. A method according to claim 1, further comprising performing two or more replicate RT-PCR analyses for the experimental sample to generate the experimental dataset.

4. A method according to claim 1, wherein filtering the control and experiment datasets comprises determining a RT-PCR cycle cut-off parameter.

5. A method according to claim 4, wherein the difference value of a data gene-normalizer gene pair is the difference in RT-PCR cycle cut-off parameters between the data gene and the normalizer gene.

6. A method according to claim 1, wherein ranking the set of data genes comprises identifying a pattern of variance between expression level of a data gene in the experimental sample and expression level of the respective data gene in the control sample.

7. A method according to claim 3, wherein ranking the set of data genes comprises quantifying the pattern of variance and ranking genes as a function of the quantified pattern of variance.

8. A method according to claim 1, wherein step (f) further comprises: performing a statistical analysis comprising:
  for each data gene-normalizer gene pair, determining whether the variation between the control difference value and the experimental difference value is statistically significant.

9. The method of claim 8, wherein the statistical analysis is a T-test.

* * * * *

UNITED STATES PATENT AND TRADEMARK OFFICE
CERTIFICATE OF CORRECTION

PATENT NO. : 7,822,556 B2  
APPLICATION NO. : 12/511493  
DATED : October 26, 2010  
INVENTOR(S) : Shreeram Akilesh, Derry Roopenian and Daniel J. Shaffer Page 1 of 1

It is certified that error appears in the above-identified patent and that said Letters Patent is hereby corrected as shown below:

Claim 7
Column 18, line 16, delete "claim 3" and insert -- claim 6 --

Signed and Sealed this
Fifteenth Day of February, 2011

David J. Kappos
*Director of the United States Patent and Trademark Office*